United States Patent
Voet

(10) Patent No.: US 6,623,742 B2
(45) Date of Patent: Sep. 23, 2003

(54) METHODS FOR TREATING FIBROMYALGIA

(75) Inventor: Martin A. Voet, San Juan Capistrano, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 09/954,610

(22) Filed: Sep. 17, 2001

(65) Prior Publication Data

US 2003/0054975 A1 Mar. 20, 2003

(51) Int. Cl.$^7$ .......................... A61K 39/08; C07K 14/33
(52) U.S. Cl. .................. 424/236.1; 424/247.1; 435/71.3; 514/2; 514/12; 530/350; 530/344
(58) Field of Search .................. 424/247.1, 236.1; 435/71.3; 514/2, 12; 530/350, 344

(56) References Cited

U.S. PATENT DOCUMENTS

| | | | |
|---|---|---|---|
| 5,437,291 A | 8/1995 | Pasricha et al. | 128/898 |
| 5,707,642 A | 1/1998 | Yue | 424/423 |
| 5,714,468 A | 2/1998 | Binder | 514/14 |
| 5,766,605 A | 6/1998 | Sanders et al. | 424/239.1 |
| 5,863,552 A | 1/1999 | Yue | 424/423 |
| 5,962,479 A | 10/1999 | Chen | 514/348 |
| 5,989,545 A | 11/1999 | Foster et al. | 424/183.1 |
| 6,009,875 A | 1/2000 | Hubbard, Jr. | 128/898 |
| 6,063,768 A | 5/2000 | First | 514/14 |
| 6,113,915 A | 9/2000 | Aoki et al. | 424/236.1 |
| 6,136,551 A | 10/2000 | Aoki | 435/7.32 |
| 6,174,880 B1 | 1/2001 | Bernstein | 514/217 |
| 6,201,022 B1 | 3/2001 | Mease et al. | 514/560 |

FOREIGN PATENT DOCUMENTS

| | | |
|---|---|---|
| WO | WO 94/15629 | 7/1994 |
| WO | WO 95/17904 | 7/1995 |
| WO | WO 99/03483 | 1/1999 |

OTHER PUBLICATIONS

Raj: *Pain Digest*, 1998; 6: 357–363, Diagnosis and Management of Fibromyalgia and Myofascial Pain Syndrome.
Wiegand et al: *Naunyn–Schmiedeberg's Arch. Pharmacol*, 1976; 292: 161–165, I–Labeled Botulinum A Neurotoxin: Pharmacokinetics in Cats after Intramuscular Injection.
Haberman: *Naunyn–Schmiedeberg's Arch. Pharmacol*, 1974; 281: 47–56, I–Labeled Neurotoxin from Clostridium Botulinum A: Preapration, Binding to Synaptosomes and Ascent to the Spinal Cord.
Mantyh: *Annals New York Academy of Science*; Part V: 263–270, Substrate P and the Inflammatory and Immune Response.
Spiegelman & Puil: *Annals New York Academy of Science*; 220–228, Substance P Actions on Sensory Neurons.
M.K. Childers et al: *Journal of Back and Musculoskeletal Rehabiitation*, 1998; 10: 89–96, Treatment of painful muscle syndromes with Botulinum toxin: A review.
Paulson et al: *Movement Disorders*, 1996; 11(4): 459, Botulinum Toxin is Unsatisfactory Therapy for Fibromyalgia.
Giladi: *Journal of Neurological Sciences*, 1997; 152: 132–135, The Mechanism of action of Botulinum toxin type A in Focal dystonia is most probably through its dual effect in efferent (motor) and afferent pathways at the injected site.
Welch et al: *Toxicon*, 2000; 38: 245–258, Sensitivity of embryonic rat dorsal root ganglia neurons to Clostridium botulinum neurotoxins.
R. Staud et al: *Pain*, 2001; 91: 165–175, Abnormal sensitization summation of second pain (wind–up) in patients with fibromyalgia syndrome.
Jerome Groopman: *The New Yorker*, Nov. 13, 2001; 78–92, Hurting all over.
Freund et al: *J Oral Maxillofac Surg*, 1999; 57: 916–920, The Use of Botulinum Toxin for the Treatment of Temporomandibular Disorders: Preliminary Findings.
Keller et al: *The Journal of Biological Chemistry*, 2001; 276(No. 16): 13476–13482, The Role of the Synaptic Protein SNAP-25 in the Potency of Botulinum Neurotoxin Type A.
Binder et al: *Movement Disorders*, 13 (Suppl 2): 241:1998, Botulinum Toxin Type A (BTX).
Siberstein et al: *Headache,* 40;445–450:2000, Botulinum Toxin Type A as a Migraine Preventive Treatment.
Relja: *Eur. Journal of Neurology*, 4(Suppl 2) S71–73: 1997, Treatment of Tension–Type Headache by Local Injection of Botulinum Toxin.
Cheshire et al: *Pain*, 59:65–69:1994, Botulinum Toxin in the Treatment of Myofascial Pain Syndrome.
Filippi et al: *Acta Otolaryngologica* 113;400–404: 1993, Effects on Rat Jaw Muscle Spindles.
Nix et al: *Neurology* 42;602–606 (1992).
Asherson, R.A., et al, *The Use of Botulinum Toxin—A in the Treatment of Patients with Fibromyalgia*, The Journal of Rheumatology 2001; Jul.; 28: 7 page 1740.

*Primary Examiner*—Christopher S. F. Low
*Assistant Examiner*—Chih Min Kam
(74) *Attorney, Agent, or Firm*—Stephen Donovan; Robert J. Baran; Carlos A. Fisher

(57) ABSTRACT

Methods for treating fibromyalgia may include administering a therapeutically effective amount of a Clostridial toxin to a peripheral location on the body of a patient. This peripheral location is other than the site on the body where the pain emanates.

32 Claims, 4 Drawing Sheets

METHODS FOR TREATING FIBROMYALGIA

BACKGROUND

Fibromyalgia is a persistent muscle pain that can be accompanied by severe fatigue, insomnia, diarrhea, abdominal bloating, bladder irritation and headache. The criteria for a diagnosis of fibromyalgia may include widespread pain throughout the body accompanied by tenderness in 11 of 18 specific tender points (FIG. 1). Tenderness is determined by applying firm pressure over each designated area.

The underlying pathophysiology and pathology of fibromyalgia is not well understood. Radiographic and histological examinations of regions associated with tenderness reveal no abnormalities. Blood chemistries, CBC, erythrocyte sedimentation rate (ESR), as well as other immunologic manifestations commonly known for other diseases (i.e. autoantibodies in Lupus), are normally negative unless there is another underlying disorder.

The source of the pain appears to be somewhat unclear. Nociceptors are present in the interstitial space between muscle fibers, in particular, on blood vessels. Studies have reported intramuscular microcirculation abnormalities as well as a decrease in energy-rich phosphates in fibromyalgia musculature, Raj et al, Pain Digest, 8(6), 357–363 (1998)). These abnormalities may be important for producing muscle associated pain since 1) impaired microcirculation results in insufficient delivery of oxygen to localized muscle regions which results in sub-optimal working capacity of the musculature which may lead to exhaustion of some motor units; and 2) reduced energy-rich phosphates (ATP and phosphorylcreatine) means that demands of working muscles are not met by the energy supply, which may cause localized muscular strain, weakness, fatigue and pain.

Fibromyalgia tender points are characterized by allodynia (a•state where a normally non-painful stimulus elicits a painful perception). Muscular dysfunction, either mechanical or metabolic, can lead to a state of sensitization of the nociceptive sensory inputs into the spinal cord altering the neurochemical balance important for nociceptive control. The process of nociception may be accomplished by a controlled release of various pro-nociceptive and anti-nociceptive agents in the nervous system. These agents include excitatory amino acids, neuropeptides, biogenic amines, nitric oxide, and prostaglandins. One important pro-nociceptive mediator is the neuropeptide substance P, which is found to be consistently elevated in the cerebrospinal fluid of fibromyalgia patients. Substance P may be released by sensory afferents arising from the muscle into the dorsal horn of the spinal cord to interact with neurokinin-1 receptors. Activation of spinal neurons by substance P prepares the neurons for an inceptive pain signal, thereby facilitating nociceptive perception. Injection of substance P into animals causes allodynia by increasing the number of afferent neurons that are activated (e.g. discharge one or more action potentials) in response to a certain nociceptive stimulus and reducing the voltage threshold needed for their activation.

A recent finding of elevated nerve growth factor levels in cerebral spinal fluid of patients may exacerbate the condition by increasing the development of substance P-containing sensory neurons, which either contribute to or accentuate the painful symptoms brought about by an elevated level of substance P. Further, levels of anti-nociceptive substances such as the neuropeptide met-enkephalin and biogenic amine serotonin are found to be significantly reduced in fibromyalgia patients' cerebral spinal fluid.

Fibromyalgia tends to be chronic and often occurs after a stressful event suffered by the patient, either physical or psychological. Current treatments involve massages, exercise, changes in diet and anti-depressant medication. All of these forms of treatment are inadequate only providing some benefit to a small subset of patients.

What is needed are new effective methods to treat fibromyalgia, including pain associated with fibromyalgia. The present invention provides methods to treat the symptoms (including pain) of fibromyalgia by the injection of a Clostridial toxin, for example, a *botulinum* toxin, into a patient at a location that is not at or near a site where the patient perceives the pain to originate. It is hypothesized that *botulinum* toxin may interfere with the central pain pathway through routes not traditionally associated with the action of this neurotoxin.

*Botulinum* Toxin

The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A ("BoNT/A") is the most lethal natural biological agent known to man. About 50 picograms of *botulinum* toxin (purified neurotoxin complex) serotype A is a $LD_{50}$ in mice. One unit (U) of *botulinum* toxin is defined as the $LD_{50}$ upon intraperitoneal injection into female Swiss Webster mice weighing 18–20 grams each. Seven immunologically distinct *botulinum* neurotoxins have been characterized, these being respectively *botulinum* neurotoxin serotypes A, B, $C_1$, D, E, F and G each of which is distinguished by neutralization with serotype-specific antibodies. The different serotypes of *botulinum* toxin vary in the animal species that they affect and in the severity and duration of the paralysis they evoke. For example, it has been determined that BoNt/A is 500 times more potent, as measured by the rate of paralysis produced in the rat, than is *botulinum* toxin serotype B (BoNT/B). Additionally, *botulinum* toxin type B ("BoNt/B") has been determined to be non-toxic in primates at a dose of 480 U/kg which is about 12 times the primate $LD_{50}$ for BoNt/A. *Botulinum* toxin apparently binds with high affinity to cholinergic motor neurons, is translocated into the neuron and blocks the release of acetylcholine.

*Botulinum* toxins have been used in clinical settings for the treatment of neuromuscular disorders characterized by hyperactive skeletal muscles. BoNt/A has been approved by the U.S. Food and Drug Administration for the treatment of blepharospasm, strabismus, hemifacial spasm and cervical dystonia. Additionally a *botulinum* toxin type B has been approved by the FDA for the treatment of cervical dystonia.

Non-serotype A *botulinum* toxin serotypes apparently have a lower potency and/or a shorter duration of activity as compared to BoNt/A. Clinical effects of peripheral intramuscular BoNt/A are usually seen within one week of injection. The typical duration of symptomatic relief from a single intramuscular injection of BoNt/A averages about three months.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* serotypes A and E both cleave the 25 kiloDalton (kD) synaptosomal associated protein (SNAP-25), but they target different amino acid sequences within this protein. BoNT/B, D, F and G act on vesicle-associated protein (VAMP, also called synaptobrevin), with each serotype cleaving the protein at a different site. Finally, *botulinum* toxin serotype $C_1$ (BoNT/$C_1$) has been shown to cleave both syntaxin and SNAP-25. These differences in mechanism of action may affect the relative potency and/or duration of action of the various *botulinum* toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the H chain and a cell surface receptor; the receptor is thought to be different for each serotype of *botulinum* toxin and for tetanus toxin. The carboxyl end segment of the H chain, $H_c$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of *botulinum* toxin activity appears to involve reduction of the disulfide bond joining the H and L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin/B/$D_x$/F, and/G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the *botulinum* toxin protein molecule, for all seven of the known *botulinum* toxin serotypes, is about 150 kD. Interestingly, the *botulinum* toxins are released by *Clostridial bacterium* as complexes comprising the 150 kD *botulinum* toxin protein molecule along with associated non-toxin proteins. Thus, the BoNt/A complex can be produced by *Clostridial bacterium* as 900 kD, 500 kD and 300 kD forms. BoNT/B and $C_1$ are apparently produced as only a 500 kD complex. BoNT/D is produced as both 300 kD and 500 kD complexes. Finally, BoNT/E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

BoNt/A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the BoNt/B serotype only cleave a portion of the toxin produced. The exact proportion of nicked to unnicked molecules depends on the length of incubation and the temperature of the culture. Therefore, a certain percentage of any preparation of, for example, the BoNt/B toxin is likely to be inactive, possibly accounting for the known significantly lower potency of BoNt/B as compared to BoNt/A. The presence of inactive *botulinum* toxin molecules in a clinical preparation will contribute to the overall protein load of the preparation, which has been linked to increased antigenicity, without contributing to its clinical efficacy. Additionally, it is known that BoNt/B has, upon intramuscular injection, a shorter duration of activity and is also less potent than BoNt/A at the same dose level.

It has been reported (as exemplary examples) that BoNt/A has been used clinically as follows:

(1) about 75–125 units of BOTOX®[1] per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U (b) flexor digitorum sublimus: 7.5 U to 30 U (c) flexor carpi ulnaris: 10 U to 40 U (d) flexor carpi radialis: 15 U to 60 U (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

[1] Available from Allergan, Inc., of Irvine, Calif. under the tradename BOTOX®.

The tetanus neurotoxin acts mainly in the central nervous system, while *botulinum* neurotoxin acts at the neuromuscular junction; both act by inhibiting acetylcholine release from the axon of the affected neuron into the synapse, resulting in paralysis. The effect of intoxication on the affected neuron is long-lasting and until recently has been thought to be irreversible. The tetanus neurotoxin is known to exist in one immunologically distinct serotype.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of the heart by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

SUMMARY

In accordance with the present invention, there are provided methods for treating fibromyalgia. These methods may include administering locally a therapeutically effective amount of a Clostridial toxin to a peripheral location on a body of a patient afflicted with fibromyalgia. The peripheral location of local administration is not a locus of pain. For example, the peripheral location may be on the body of a patient about one centimeter or more from the locus of pain. In one embodiment, the locus of pain is a fibromyalgia tender point.

In one embodiment of the present invention, a dermatome may include both the locus of pain, for example, where a pain associated with fibromyalgia is perceived by the patient to originate, and the peripheral location where the therapeutically effective amount of a Clostridial toxin is administered.

In another embodiment, the peripheral location where an effective amount of Clostridial neurotoxin is administered is in the head of the patient. For example, the neurotoxin may be administered to the facial area and/or cranial area of the head. In this embodiment, where an effective amount of Clostridial neurotoxin is administered in the head of the patient, the locus of pain to be treated is not in the head. For example, the locus of pain may be at a fibromyalgia tender point.

Further in accordance with the present invention, there are provided methods for treating pain which may include administering locally a therapeutically effective amount of a Clostridial toxin to a peripheral location on a body of a patient. The site of local administration is other than a locus of pain. A dermatome may include both a locus of pain and a site of local administration. In one embodiment, the locus of pain may be at a fibromyalgia tender point. In one embodiment, a patient has at least eleven loci of pain.

Further in accordance with the present invention, there are provided methods for treating fibromyalgia. These methods may include administering locally a therapeutically effective amount of a Clostridial toxin to a dermatome of a patient afflicted with fibromyalgia. This dermatome may substantially include a locus of pain. The local administering is not at a locus of pain. In one embodiment of the invention, the locus of pain is at one or more fibromyalgia tender points.

Methods for treating pain are within the scope of the invention. These methods may administering locally a therapeutically effective amount of a Clostridial toxin at a location in a dermatome other than a locus of pain. This dermatome also includes a locus of pain. The locus of pain may be at a fibromyalgia tender point.

Further in accordance with the present invention, there are provided methods for treating fibromyalgia pain. These methods include a step of administering a therapeutically effective amount of *botulinum* toxin type A to a dermatome. This dermatome may include a site where the pain is perceived by the patient to originate.

Still further in accordance with the present invention, there are provided methods for treating pain which is perceived to originate at fibromyalgia tender point. These methods include a step of administering a therapeutically effective amount of *botulinum* toxin type A to a location in a dermatome other than where the pain is perceived to originate. This dermatome includes the site where the pain is perceived to originate.

A toxin used in accordance with the present invention may be *botulinum* toxin type A, B, $C_1$, $C_2$, D, E, F, G or fragments of these toxins or derivatives of these toxins. In one embodiment of the present invention, the toxin may be a mixture or combination of these *botulinum* toxins.

The location where the therapeutically effective amount of a toxin is administered and the site where a pain is perceived by the patient to originate may have neuronal processes that project from the same spinal sensory nerve root.

Further in accordance with the present invention, a toxin may be administered, for example, subcutaneously or intramuscularly. Further, the toxin may be administered with a needle or by needleless injection.

In one embodiment of the present invention, there is provided a method for treating fibromyalgia which may include administering locally a therapeutically effective amount of a *botulinum* toxin type A to a dermatome of a patient afflicted with fibromyalgia. The dermatome substantially encompasses a locus of pain and the locus of pain is at a fibromyalgia tender point. The local administration is not at the locus of pain.

In one embodiment of the present invention, there is provided a method for treating pain which may include administering locally a therapeutically effective amount of a *botulinum* toxin type A to a dermatome of a patient. The patient has a locus of pain which is at a fibromyalgia tender point, wherein the dermatome substantially encompasses the locus of pain, and wherein the local administration is not to the locus of pain.

Any and all features described herein and combinations of such features are included within the scope of the invention provided that such features of any such combination are not mutually exclusive.

These and other aspects and advantages of the present invention are apparent in the following detailed description and claims.

Definitions

"Administering locally" means administering a pharmaceutical by a non-systemic route, such as by intramuscular or subcutaneous injection or implantation of a suitable implant. Thus, for example, oral and intravenous routes of administering are excluded from the scope of "administering locally."

"Clostridial toxin" means a toxin produced naturally by the genus of bacteria Clostridium. For example, Clostidial toxins include, but are not limited to, *botulinum* toxins, tetanus toxins, difficile toxins and butyricum toxins. A Clostridial toxin can also be made by known recombinant means by a non-*Clostridial bacterium*.

"Combination" means an ordered sequence of elements. For example, a combination of *botulinum* toxins may mean administration of *botulinum* toxin E, followed by administration of *botulinum* toxin type A, followed by administration of *botulinum* toxin type B. This is opposed to a "mixture" where, for example, different toxin types are combined prior to administration.

"Dermatome" means a segment of a human body innervated by a single dorsal root. Dermatomes follow a highly regular pattern on the body (FIG. 3) and are categorized into four major regions, the cervical (C), the thoracic (T), the lumber(L) and the sacral (S) regions (FIG. 3). A dermatome may substantially encompass a locus of pain.

"Derivative" means a chemical entity which is slightly different from a parent chemical entity but which still has a biological effect similar, or substantially similar, to the biological effect of the chemical entity. The biological effect of the derivative may be substantially the same or better than that of the parent. For example, a derivative neurotoxin component may have one or more amino acid substitutions, amino acid modifications, amino acid deletions and/or amino acid additions. An amino acid substitution may be conservative or non-conservative, as is well understood in the art. In addition, derivatives of neurotoxin components may include neurotoxin components that have modified amino acid side chains, as is well known in the art.

An example of a derivative neurotoxin component may comprise a light chain of a *botulinum* toxin having one or more amino acids substituted, modified, deleted and/or added. For example, a derivative light chain may have the same or an increased ability to prevent exocytosis compared to the native light chain. For example, preventing the release of neurotransmitter vesicles. Additionally, the biological effect of a derivative may be decreased compared to the parent chemical entity. For example, a derivative light chain of a *botulinum* toxin type A having an amino acid sequence removed may have a shorter biological persistence than that of the parent (or native) *botulinum* toxin type A light chain.

"Fibromylagia tender point" or "tender point" means an area of a human body which when firm even, pressure is applied pain may result. Elicitation of pain from 11 of 18 fibromyalgia tender points, by application of firm even pressure, results in a diagnosis of fibromyalgia. FIG. 1 shows the location of the tender points. They are: a) occiput, suboccipital muscle insertions; b) trapezius, midpoint of the upper border; c) supraspinatus, above the medial border of the scapular spine; d) gluteal, upper and outer quadrant of buttocks; e) greater trochanter, posterior to the trochanteric prominence; f) low cervical, anterior aspects of the intertransverse spaces; g) second rib, second costochondral junctions; h) lateral epicondyle, 2 centimeters distant to the epicondyles; and i) knee, medial fat pad proximal to the joint line.

"Fragment" means a portion of an amino acid sequence that comprises five amino acids or more of the native amino acid sequence up to a size of minus at least one amino acid from the native sequence. For example, a fragment of a

*botulinum* toxin type A light chain comprises five or more amino acids of the amino acid sequence of the native *botulinum* toxin type A light chain up to a size of minus one amino acid from the native light chain.

"Locus of pain" means a site or location on a body of a patient where the patient perceives that a pain is emanating from and/or a site or location on a body of a patient where application of pressure results in pain. For example, a locus of pain may be at a fibromyalgia tender point. Furthermore, a locus pain may have certain discrete physical boundaries. For example, a locus of pain may include a dermis area of less than about 4 cm$^2$, 12 cm$^2$, 40 cm$^2$ or 60 cm$^2$. The locus of pain may extend to tissues directly below the dermis area. For example, the locus of pain may extend about 0.5 cm, 1.0 cm, 2 cm, 4 cm or 6 cm below the dermis area.

"Needleless injection" means injecting a measurable amount of substance, for example, a carrier coated with a *botulinum* toxin without the use of a standard needle.

"Neurotoxin" means a chemical entity (i.e. a molecule) that is capable of interfering with or influencing a function of a neuron or other target cell. For example, a neurotoxin may interfere with the transmission of an electrical signal from a nerve cell to its target. The target may be, for example, another nerve cell, a tissue or an organ. The "neurotoxin" may be naturally occurring or synthetic.

"Peripheral location" means a site on or in the periphery of a mammals' body, such as in or under the skin or a skeletal muscle. Peripheral location excludes a site within the viscera or in the central nervous system.

"Substantially" means largely but not entirely. For example, substantially encompassing may mean encompassing 10%, 20%, 30%, 40% or 50% or more.

DESCRIPTION

The present invention relates to methods for treating fibromyalgia. In one embodiment, the invention relates to methods for treating pain associated with fibromyalgia and pain associated with fibromyalgia tender points.

It has been reported that *botulinum* toxin is ineffective to treat fibromyalgia, see Paulson et al, Mov Dis 11(4), 459 (1996) and Childers et al, Musculoskeletal Rehabilitation 10, 89–96 (1998). In these reports, *botulinum* toxin was injected into the site of fibromyalgia associated pain (shoulder muscles). George Paulson, co-author of one above cited article, has stated; "Based on our experience, we suggest that patients with fibromyalgia are unlikely to benefit from *botulinum* toxin injection" (Paulson et al).

Methods for treating a symptom of fibromyalgia (including pain) by non-systemic administration of a therapeutic amount of neurotoxin are within the scope of the present invention. In one broad embodiment of this invention, a neurotoxin is administered to a site on the body of a patient other than a site where the pain to be treated is perceived to originate. For example, a neurotoxin may be administered to a site other than a tender point to be treated in association with fibromyalgia.

Figure 1:
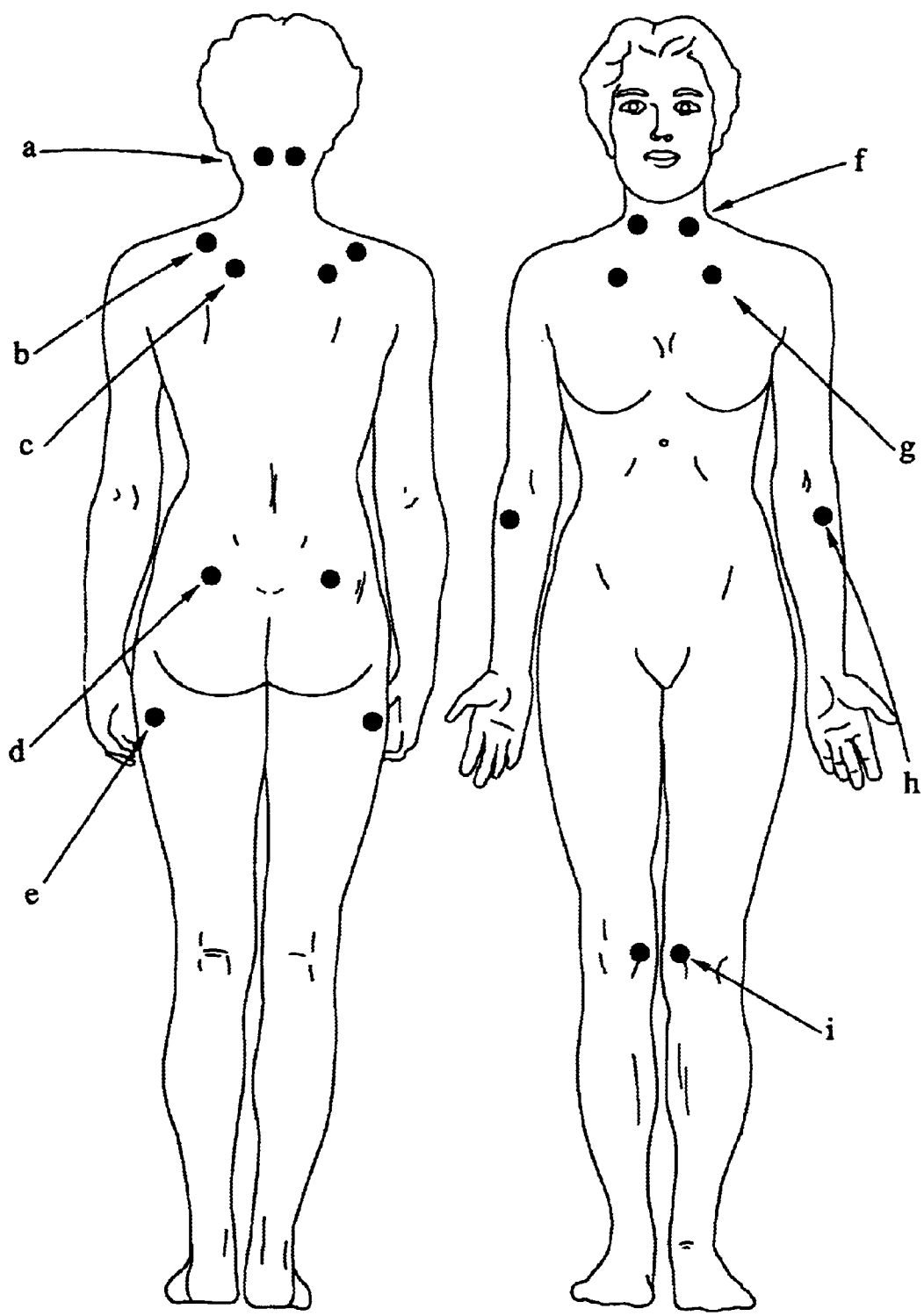
FIG. 1 shows the location of fibromyalgia tender points.

The locations of fibromyalgia tender points are shown in FIG. 1. Pain may be perceived to originate from these locations in a fibromyalgia patient. The pain may be centered at these, or other sites and may be accompanied by an emanating diffuse pain. In one embodiment, pain may be perceived to originate at a location on a body if the location is pain sensitive when firm, even pressure is applied.

Preferably, the neurotoxin used to practice a method within the scope of the present invention is a Clostridial toxin, or fragments thereof, or derivatives thereof. For example, *botulinum* toxin serotypes A, B, C, D, E, F or G may be used. Because of reasons including its high potency in humans and ready availability, the *botulinum* toxin preferably used is *botulinum* toxin type A.

Without wishing to be limited to any theory or mechanism of operation, it is hypothesized that pain pathways and/or pain feedback loops are influenced by neurotoxins, for example, *botulinum* toxins, administered in accordance with the present invention. For example, neurotoxins may act through the afferent nerve pathways to block the release of pain transmitters, for example, substance P. This mechanism of operation may be related to that by which peripheral administration of *botulinum* toxin is known to alleviate pain associated with migraine headache, see Binder, U.S. Pat. No. 5,714,468; Yue, U.S. Pat. No. 5,863,552; First, U.S. Pat. No. 6,063,768; Yue, U.S. Pat. No. 5,707,642; Sanders, U.S. Pat. No. 5,766,606; and Aoki, U.S. Pat. No. 6,113,915. The disclosure of these patents is herein incorporated in its entirety by reference.

Figure 2:
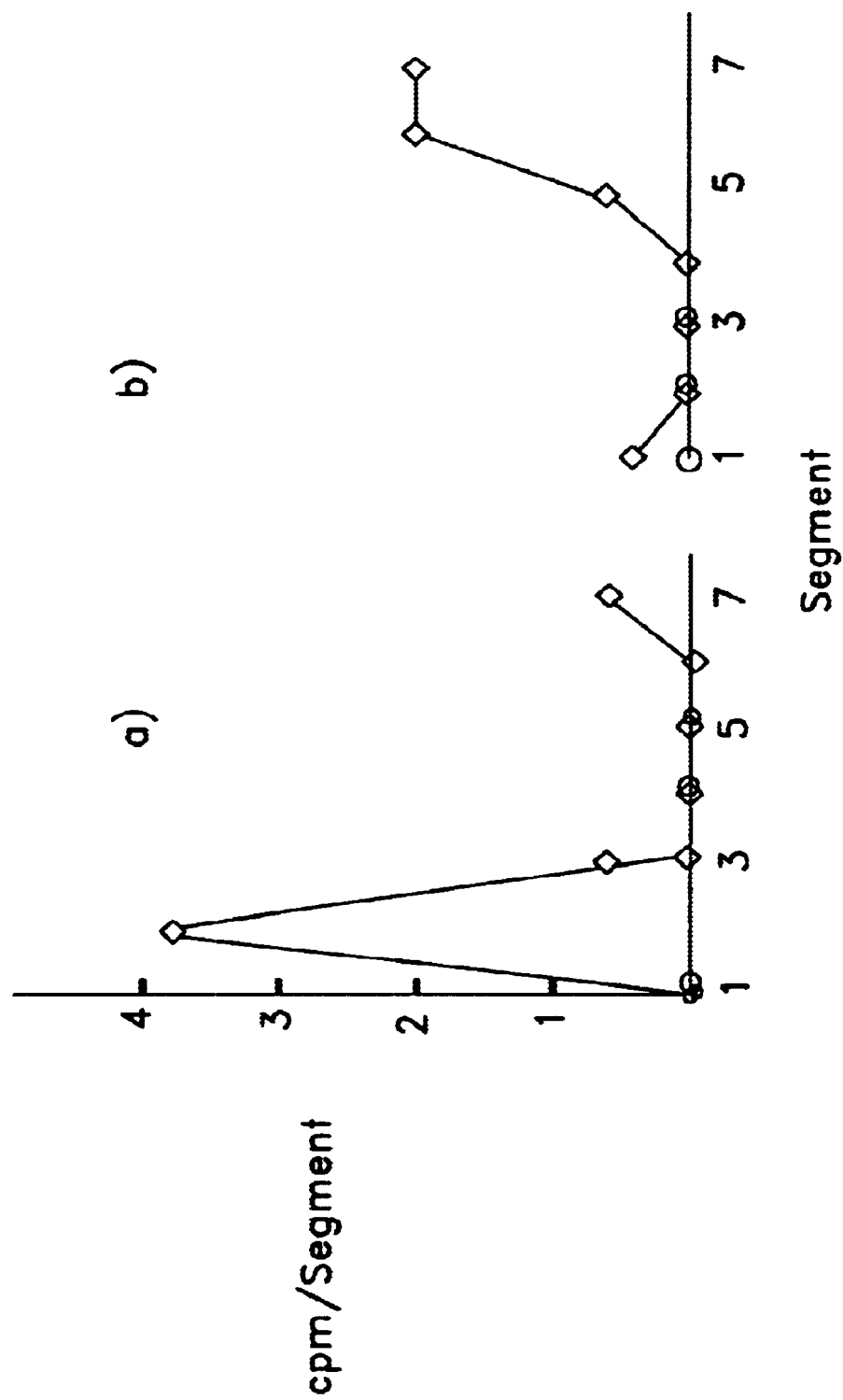
FIG. 2 shows the segmental accumulation of radiolabeled *botulinum* toxin in the spinal cord of a rat. (From Habermann, Naunyn-Schmiedeberg's Arch Pharmacol 281, 47–56 (1974)).

In support of this theory, treatment of pain by intraspinal administration of *botulinum* toxin has been proposed. See Aoki et al, U.S. Pat. No. 6,136,551 and Foster et al, U.S. Pat. No. 5,989,545. The disclosure of these patents is herein incorporated in its entirety by reference. Further, neurotoxins, for example, *botulinum* toxin type A, have been shown to be retrogradely transported to the spinal cord following injection of the toxin into either the hind limb or forelimb of a rat (Habermann, Naunyn-Schmiedeberg's Arch Pharmacol. 281, 47–56 (1974), incorporated herein in its entirety by reference). In this study, dialyzed, radiolabeled *botulinum* toxin (about 0.2 ug/ml) was injected into either the left gastronemius or the left foreleg of rats in a volume of 0.2 ml/100 g body weight. All animals were killed and their spinal cords removed and radiolabeled *botulinum* toxin was quantitated. The results suggest that *botulinum* toxin ascends to the spinal area by retrograde transport (FIG. 2). Further, Wiegand et al, Naunyn-Schmiedeberg's Arch Pharmacol 292, 161–165 (1976), incorporated herein in its entirety by reference, have also shown that radiolabeled *botulinum* toxin travels to the spinal cord after intramuscular injection. Wiegand et al state that: "obviously the [radiolabeled *botulinum* toxin] reaches the spinal cord by neural ascent via the ventral roots." Several findings by Wiegand et al support this hypothesis. For example, after injection of the labeled toxin, a gradient of radiolabel was found to form in the sciatic nerve. In addition, a significant level of radioactivity was found in the ventral roots giving rise to the innervation of the injected muscle. Also, this radioactivity was localized exclusively within the axons of the neurons. Further, a ligature of the left ventral root prevented the radiolabeled *botulinum* from reaching the corresponding segment of the spinal cord half segment.

The idea that *botulinum* toxins move through the afferent nerve pathways by retrograde transport is further supported by the distant effect *botulinum* toxin may have when administered by intramuscular or subcutaneous injection. For example, there is electrophysiological evidence that *botulinum* toxin type A can effect muscle spindle output, by the Ia afferent signal, Filippi et al, Acta Otolaryngologica 113, 400–404 (1993). Remote effects of *botulinum* toxins at distant body parts have been reported by Nix et al (Neurology 42, 602–606 (1992)). In addition, it has been proposed that the mode of action of *botulinum* type A on focal dystonias is through the afferent pathways in addition to the well-known effect at the alpha motor neuron nerve terminals, Giladi, J of Neuro Sci 152, 132–135 (1997). Each of these publications is incorporated herein in its entirety by reference. It is possible that part of the mechanism of action of *botulinum* toxin in treating focal dystonias is that retrograde transport of the toxin to the spinal area takes place and inhibition of the release of pain producing substances results, for example, inhibition of substance P release. In support of this, *botulinum* toxins have been shown to markedly inhibit the release of substance P in neuron cell cultures, Welch et al, Toxicon 38, 245–258 (2000). The ability of a neurotoxin, for example, a *botulinum* toxin, to inhibit the release of a pain producing substance at a location in the body distant to the site of administration of the toxin is important for at least one theory of operation of the present invention.

Without wishing to limit the invention to any theory or mechanism of operation, it is hypothesized that the afferent nerve pathways innervating the tissue at the point of origin of certain types of pain, for example pain associated with fibromyalgia, may be effected in a manner so as to disallow the effect of a neurotoxin, for example, a *botulinum* toxin, on the release of pain producing substances. For example, the ability of a *botulinum* toxin to move by retrograde transport in afferent pathways may be blocked. The present invention allows for bypassing a blockage by administration of the neurotoxin to a location that is not at or near the site of pain origin. For example, the neurotoxin may be administered to a location on a body other than a site on the body where a pain is centered. The toxin may then move by retrograde transport up the afferent neural pathway and into the spine where a local or regional inhibition of release of pro-nociceptive mediators, for example substance P, may take place. Release of nociceptive mediators into the dorsal root that leads to innervation of the site of pain may be inhibited resulting in a subsidence of pain, for example, subsidence of pain at the origin of the pain. Further, it may be preferable to administer the neurotoxin to a region of a body that is innervated by the same dorsal root that innervates the site of pain to be treated. Doing so may allow for the most direct route for the toxin to reach the sensory neurotransmitters associated with the site of pain.

The data of Habermann and Wiegand et al show a segmental distribution of *botulinum* toxin accumulation in the spinal cord of rats after intramuscular injection. The distribution was determined by the innervation of the muscles which were injected with the toxin. The graphs of FIG. 2 show the accumulation of radioactivity in the spinal cord following injection of the toxin. Graph A shows the results for injection into the hind limb and graph B shows the results for injection into the forelimb. The X-axis of each graph represents the segment of the rat's spinal cord examined for radioactive deposit. It can be seen that an injection of the labeled toxin into the hind limb causes radioactivity to appear in lumbar segment 2 of the cord, whereas an injection into the forelimb results in deposit of radioactivity in cervical segments 6 and 7 of the cord.

Figure 3:
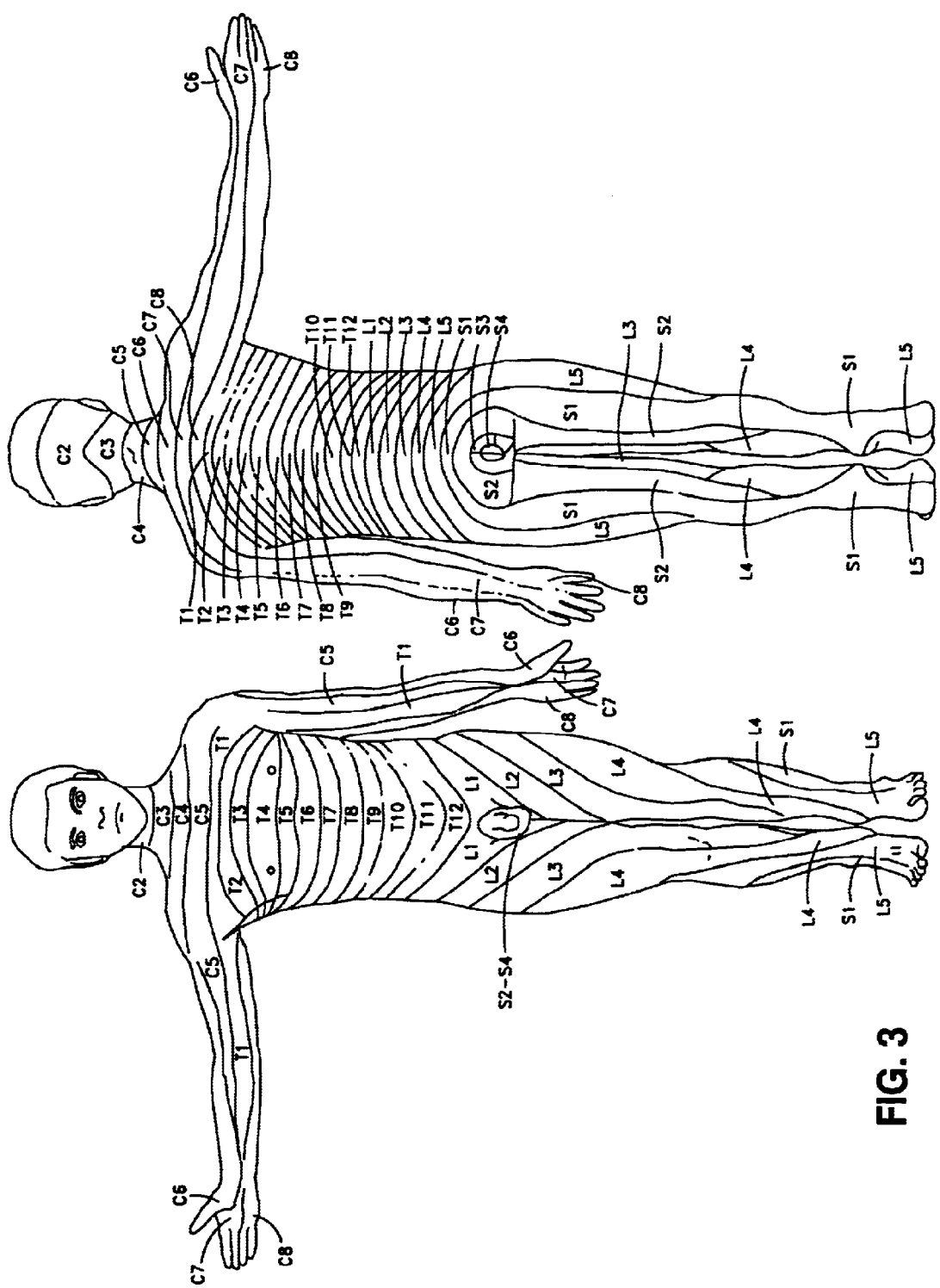
FIG. 3 shows the location of human dermatomes.

Segments of a human body innervated by a single dorsal root are known as dermatomes (FIG. 3). Since one dorsal root may innervate a single dermatome, a neurotoxin, for example, a *botulinum* toxin, may be administered to a location at or near a dermatome encompassing a site of pain to be treated. In one embodiment of the invention, the neurotoxin is administered to a dermatome that encompasses the site, or point of origin, of pain to be treated, for example, a fibromyalgia tender point. In this embodiment, the neurotoxin is administered to a location on the body of the patient that is not at or near the site of pain origin.

Figure 4:
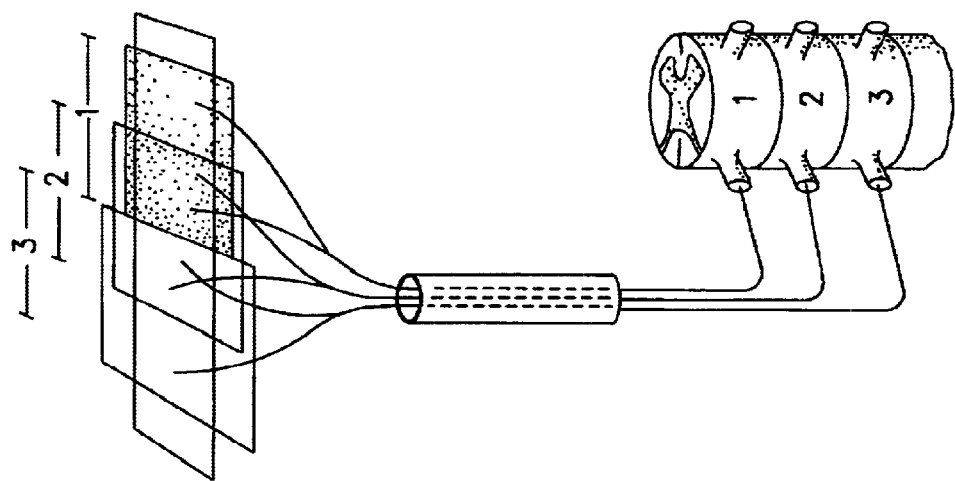
FIG. 4 shows three spinal cord segments with their corresponding dorsal roots innervating three common areas of a skin.

Dermatomal boundaries may overlap as is shown in FIG. 4. Therefore administration of toxin into a dermatome that does not encompass the site of pain origin to be treated may be effective. Therefore, in one embodiment of the invention, the neurotoxin is administered to a dermatome that is adjacent to the dermatome which contains the site of pain origin. In another embodiment of the invention, the neurotoxin is administered to a dermatome that is one or more dermatomes away from the dermatome which contains the site of pain origin.

In one broad embodiment, the neurotoxin may be administered to a site on the body of a patient that is about 0.1 centimeters or more from the site of pain origin. In another embodiment, the neurotoxin may be administered to a location on the body of a patient that is about 1 centimeter or more from the site of pain origin. In another embodiment, the neurotoxin is administered to a location on the body of a patient that is about 4 centimeters or more from the site of pain origin. In still another embodiment of the invention, the neurotoxin is administered to a location on the body of a patient that is about 8 centimeters or more from the site of pain origin. In still another embodiment of the invention, the neurotoxin is administered to a location that is about 0.1 centimeter to less than about 200 centimeters from the site of pain origin. In still another embodiment of the invention, the neurotoxin is administered to a location that is about 1 centimeter to less than about 6 centimeters from the site of pain origin. In still another embodiment of the invention, the neurotoxin is administered to a location that is about 3 centimeter to about less than about 100 centimeters from the site of pain origin.

Generally, the dose of neurotoxin to be administered will vary with the age, presenting condition and weight of the patient to be treated. The potency of the neurotoxin will also be considered. Toxin potency is expressed as a multiple of the $LD_{50}$ value for a mouse. One "unit" of toxin can be defined as the amount of toxin that kills 50% of a group of mice that were disease-free prior to inoculation with the toxin. For example, commercially available *Botulinum* toxin A typically has a potency such that one nanogram contains about 40 mouse units. The potency, or $LD_{50}$ in humans of the *Botulinum* toxin A product supplied by Allergan, Inc. under the registered trademark "BOTOX" is believed to be about 2,730 mouse units.

The neurotoxin can be administered in a dose of about 0.1 units up to about 1,000 units. In one embodiment, individual dosages of about 15 units to about 30 units are used. In another embodiment, individual dosages of about 30 units to about 60 units are used. In still another embodiment, individual dosages of about 60 units to about 180 units are used. Generally, the neurotoxin will be administered as a composition at a dosage that is proportionally equivalent to about 2.5 cc/100 units. Those of ordinary skill in the art will know, or can readily ascertain, how to adjust these dosages for neurotoxin of greater or lesser potency.

Preferably, the lowest therapeutically effective dosage will be injected into the patient. The lowest therapeutic dosage is that dosage which results in detection by the patient of a reduction in the occurrence and/or magnitude of pain experienced by the patient, for example, pain experience by a patient which is associated with fibromyalgia.

Methods for assessing or quantifying the amount of pain experienced by a patient are well known to those skilled in the art. For example, a patient can be given a pain assessment test in which the patient quantifies the degree of pain based on a scale. One example would be assigning the patient's pain a number based on a scale of 1 to 10, where a "10" would indicate the worst degree of pain the patient might imagine. A pain measure of 4 from an original pain score of 8 would be a 50% reduction in pain. Thus, the amount of conjugate required to achieve that 50% reduction in pain could be considered 1 U of the *botulinum* toxin component-targeting moiety conjugate. Alternatively, the patient's pain may be measured as the duration of pain. One unit of the conjugate of the invention would accordingly reduce the duration of pain by 50%. In addition, a number of physiological measures, such as heart rate, respiratory rate, blood pressure, and diaphoresis, may be used alone or together with the patientive methods described above, to quantify the amount of the patient's pain.

In an initial treatment, a low dosage may be administered at one site to determine the patient's sensitivity to, and tolerance of, the neurotoxin. Additional injections of the same or different dosages will be administered as necessary. For example, if pain predominates in the shoulder region (FIG. 1), the patient may receive about 40 units in the cervical region, for example, in dermatome C7. In one embodiment, the patient receives 40 units in the C7 dermatome of the cervical region and may also receive 40 units of the neurotoxin in the C8 and/or C6 dermatomes.

In one embodiment, the site of injection is intramuscular. However, for some indications, extramuscular injection may be the most efficacious route of administration as well as a route which avoids the risk of trauma to muscle tissue. Such injection may, for example, be made subcutaneously or, preferably, perivascularly (to produce infiltration of the neurotoxin into innervated tissue). In one embodiment, the site for injection of the neurotoxin is in or near the extramuscular regions.

The neurotoxins may be administered by, for example, injection using a needle or by needleless injection.

In needleless injection delivery methods, microprojectile drug particles may be coated with a neurotoxin and then discharged into the skin from an external delivery device. Depending on the discharge velocity and the distance from the injection site, the drug particles penetrate through the stratum corneum to different layers of the epidermis, dermis and underlying muscle. As the microprojectiles penetrate through epidermal and dermal cells, or are deposited in these cells, the neurotoxin is released. Individual layers of skin cells or underlying muscle cells may be targeted for the microprojectiles.

For intramuscular injections using a needle, to ensure that the neurotoxin is delivered to the target site without substantial systemic distribution, electromyographical ("EMG") injection may be used. A preferred technique for EMG injection is to introduce the neurotoxin through a monopolar hollow bore needle (commonly, one which is coated with a non-stick surface such as "TEFLON®", a trademarked product of DuPont Nemours, of Mass.). The needle is placed through the skin and into the target site of a muscle, preferably at a neuromuscular junction. Once the needle has been inserted, the most active site of the muscle can be determined by observation of the EMG signal. Those of ordinary skill in the art will know of, or can readily ascertain, other suitable techniques for administering EMG injections.

The injections will be repeated as necessary. As a general guideline, *Botulinum* toxin A administered into or near muscle tissue according to the method of the invention has been observed to produce flaccid paralysis at target site muscles for up to about 3 to about 6 months. Reduction of pain, for example, pain associated with fibromyalgia, in patients who received the neurotoxins of the invention extramuscularly may persist for extended periods of time. However, *botulinum* toxin type A in particular is expected to be most effective when administered according to the method of the invention at about 3 month intervals.

The invention having been fully described, examples illustrating its practice are set forth below. These examples should not, however, be considered to limit the scope of the invention, which is defined by the appended claims.

EXAMPLES

Example 1

A 37-year old woman complains of pain "all over," specifically in the occiput, neck, shoulders, lower back, hips, and right leg.

At the time of evaluation, the patient complains specifically of occipital headache, which she describes as burning and aching. She complains of neck pain and stiffness. Aching pain in the upper back and shoulders is constant, as is pain in a band-like fashion across the lower back. She also notes a great increase in her upper back and neck pain. The patient injures her lower back one year prior to this evaluation—while working as a nurse's aide as she transfers a patient. She subsequently continues to experience lower back, hip, and right leg pain and stiffness.

The patient reports a high level of anxiety and stress in her life which she feels is due to her separation and pending divorce from her husband, as well as a worsening of her pain. Her sleep is interrupted by pain several times nightly and a general lack of energy is reported.

Upon examination, it is found that the patient tests positive for pain sensitivity in 11 of the 18 fibromyalgia tender points (FIG. 1). Specifically, tenderness is present in the left and right occiput, the left and right cervical regions, the left and right trapizious, the left and right gluteal, the left and right supraspinatus and the right greater trochanter. A diagnosis of fibromyalgia is made.

The patient is treated by intramuscular injection of 40 units of *botulinum* toxin type A into each of dermatomes C3, C5, C8, L3 and L5. Each of these dermatomes includes, or is adjacent to, a positive testing tender point. Each injection is no closer than one centimeter to a tender point. Within one week of treatment, the patient notes a substantial decrease in pain felt throughout her body. Most notable is the decrease in pain associated with the tenderpoints. The patient now notes little discomfort when pressure is applied to these points. Pain relief lasts for approximately four months.

Example 2

A physical examination reveals a slender 38-year old woman in no distress. The patient walks with a normal gait and is able to perform heel walk and toe walk without difficulty. Range of motion of the lumbar and cervical spine is complete but painful in extremes of range. Motor and sensory examination of the upper and lower extremities reveals mild S1 sensory loss on the right side. Reflexes are intact at the knees and ankles. Straight leg raise is negative. Further examination reveals the presence of multiple tender points in the occipital, lower cervical, trapezium, gluteal, and greater trochanter areas bilaterally.

Radiographics of the cervical and lumbar spine are essentially normal demonstrating only mild degenerative changes. Past medical history includes asthma and hypertension. Past surgical history includes repair of a uterine rupture.

A physician applies firm, even pressure sequentially to the 18 fibromyalgia tender points and notes a positive pain sensitivity in 12 of the points. The patient is diagnosed with fibromyalgia. She is treated with subcutaneous injections of 60 units of *botulinum* toxin type A approximately 5 centimeters from the occipital, lower cervical, trapezium, gluteal, and greater trochanter tender points (FIG. 1). After approximately 6 days the patient reports herself to be pain free. The patient also reports little impairment to her mobility as a result of the *botulinum* toxin injection. The relief from pain lasts approximately 6 months at which time the injections are repeated.

Example 3

A 37 year old woman visits a sleep clinic. She reports a 5 months history of nocturia, active and exhaustive dreaming, and daytime sleepiness. Two months prior to this visit the woman visits another clinic for an evaluation of unrestful sleep. At this clinic, she is prescribed sleep medication (Benadryl) which has little effect. The patient complains of general fatigue and "muscular achiness", which she attributes to her lack of sleep. The pain felt by the patient appears to radiate from specific points on the patient's body. These points include fibromyalgia tender points of the left and right knees, left and right gluteal, left and right trapezius and the left and right occiput, left and right low cervical, and left and right second ribs. The patient shows sensitivity when firm pressure is applied to these points. The patient reports high stress and anxiety as a result of going through a "painful" divorce eight months prior to the onset of symptoms. A diagnosis of fibromyalgia is made, for which the patient is prescribed amytriptyline (Elavil®). Despite improvement in sleep, the muscle pain persists. In the previous month, the pain the patient experiences negatively impacts her work performance.

The patient is treated by intramuscular injection of 30 units of *botulinum* toxin into each of dermatomes L4, S1, C7 and C3. All injections are about four centimeters from a site of a diagnosed fibromyalgia tender point. One week after treatment the patient reports approximately a 50% reduction in pain which lasts for approximately 4 months.

Example 4

A 28 year old woman is referred to a rheumatology clinic from her HMO primary care physician after she complains of diffuse muscle pain that is centered in her trapezium, subscapularis, gluteal, and greater trochanteric regions. The pain persists for over 4 years with an increase in pain in the past six months. The patient also reports unrestful sleep characterized by excessive dreams, sensitivity to noise and light, and nocturia. Through her professional school education (the patient is a licensed medical technologist), a self diagnosis of fibromyalgia is made, and through a family friend, she obtains a prescription for Elavil®. Initially, the Elavil® helps the patient sleep which may reduce some muscle soreness. Recently, however, much of the drug's effectiveness has been lost. Up to two months prior to this office visit, the patient is on 100 mg Elavil® at bedtime, which is supplemented with 25 mg Prozac® in the morning. When the patient discovers that she is pregnant, she ceases taking all medications. Since then, the pain worsened. Due to the relative safety of localized intramuscular injection of *botulinum* toxin during pregnancy, *botulinum* toxin injection treatment is recommended. Three subcutaneous injections, of 10 units of *botulinum* toxin type A are made into each of the dermatome regions C7, C8, L5 and S1. All injections are made about 6 centimeters from the area where pain is centered. Over a two week period, pain is completely alleviated. The patient reports an improvement in sleep pattern and an overall sense of well being. Cessation of pain lasts for 3 months at which time the injections are repeated.

Example 5

A 30 year old coal miner visits his family physician with chief complaints of persistent pain in the upper and lower back, "numbness" of the hands and feet, and sensation of swollen hands. Upon questioning, the man discloses bouts of gastrointestinal discomfort, both before and after meals. The patient denies any drug use or cigarette smoking, except for an occasional alcoholic drink. He also denies any disturbance in sleep, except sometimes the headaches keep him up "all night long." Visual observation reveals a man not under distress, and examination of the hands found no evidence of swollenness. Cranial tests are normal. Reflexes are normal. Palpation at 5 different areas along the axial spine, including the shoulder, occipital, and gluteal regions reveal slight tenderness with moderate pressure. No tenderness is found in any other locations. A blood chemistry is ordered. With an exception of a slightly lower K+ level, all other values are normal. Antinuclear antibody, rheumatoid factor, creatine kinase, magnesium, lyme titre, and thyroid function tests are negative. A diagnosis of fibromyalgia is inappropriate since only 5 of the 11 fibromyalgia tender points are pressure sensitive. The physician prescribes intramuscular injections of 10 units of *botulinum* toxin type A into the sternocleidomastoid and gluteus maximus. Each injection is made about 3 centimeters from a site of tenderness. After one week, the patient reports only mild relief. Further injections are made in the sclaneus anterior, serratus anterior, lattismus dorsi, quadriceps femoris, and semitendinosus. Pain relief, including persistent headaches and irritable bowel, is realized one week after this treatment.

Example 6

A 34-year-old woman seeks medical attention for generalized pain throughout her body which she perceives as originating from numerous locations. The patient reports the symptoms persisting for the past 5 months. In addition, the patient reports feelings of fatigue and an inability to obtain restful sleep. She also states that she has been under extreme stress during the past two years resulting from working full time and raising four children. In addition, approximately one year before the onset of symptoms, the patient is in an automobile collision where she receives internal injuries to her spleen which is subsequently removed. Physical examination reveals the presence of 14 fibromyalgia tender points on her body showing pain sensitivity when firm pressure is applied to them. These sites include the left and right low cervical, left and right second rib, left and right gluteal, left and right trapezium, left and right knee, right greater trochanter, left lateral epicondyle and left and right occiput regions. A diagnosis of fibromyalgia is made. The patient objects to the prescribing of antidepressants for the condition and refuses the medication.

The fibromyalgia associated pain is treated with injection of 20 units of *botulinum* toxin type A, B, $C_1$, $C_2$, D, E, F or G into dermatomes encompassing, or into dermatomes adjacent to dermatomes encompassing, the sites of tenderness. These dermatomes are C3 T2, L5, C6, L3, L5, T1 and C3. All injections are subcutaneous and are made about 4 centimeters from the site of the tender point.

At 1 week a physical examination reveals no sign of fibromyalgia related pain.

Example 7

A patient, age 45, presents a pain in the upper chest which corresponds to the second rib region. The patient reports this specific point of pain to be the source of a general, diffuse pain that is present in the patient's upper body. The patient reports no other symptoms. The patient is treated by an injection of a modified neurotoxin intramuscularly to the T2 dermatome approximately 20 centimeters from the origin of the pain. Preferably, the modified neurotoxin is a modified *botulinum* type A, B, $C_1$, $C_2$, D, E, F or G. The particular dose as well as the frequency of administrations depends upon a variety of factors within the skill of the treating physician. Within 1–7 days after modified neurotoxin administration the patient's pain is substantially alleviated. The duration of the pain alleviation is from about 1 to about 6 months.

Example 8

Upon examination, a 56 year old woman presents the presence of multiple tender points including those in the occipital, lower cervical, trapezium, gluteal, and greater trochanter areas bilaterally and in the left knee. Pain is perceived to originate at the tender points and emanate from them forming a diffuse pain. The patient also reports symptoms of irritable bowel and fatigue. She states that she has been suffering from these symptoms for over a year and that just recently the pain she has been experiencing increases substantially. The patient undergoes surgery to repair torn cartilage in the left knee joint approximately one year prior to the onset of the symptoms. The patient is treated by subcutaneous injection of a modified neurotoxin to sites within dermatomes that contain the tender points. The injections are made about 6 centimeters from the site of the tender points. The modified neurotoxin is, for example, a modified *botulinum* toxin type A, B, C1, C2, D, E, F and/or G. The modified neurotoxin may comprise, for example, a leucine-based motif and/or additional tyrosine-based motifs and/or sites of phosphorylation. The particular dose as well as the frequency of administration depends upon a variety of factors within the skill of the treating physician, as previously set forth. Within 1–7 days after modified neurotoxin administration the patient's pain is substantially alleviated. The duration of the pain alleviation is from about 7 to about 27 months.

Example 9

A 36 year old woman has a 15 year history of chronic pain in the upper torso area. Fifteen years prior to evaluation she notes a decrease in mobility in her left elbow and knees. The pain in the left side of her body is thought to be worse than in the right. Upon examination it is revealed that the patient is pain sensitive to firm pressure that is applied sequentially to thirteen of the eighteen fibromyalgia tender points. She is diagnosed as having fibromyalgia and is treated with antidepressant medication including amytriptyline (Elavil). The medication has little effect on the level of pain experienced by the patient.

The patient is injected with *botulinum* toxin type A at locations on the body approximately nine centimeters from the center points of fibromyalgia associated pain. Each injection is made within a dermatome that des not encompass the source of the pain. The particular dose as well as the frequency of administrations depends upon a variety of factors within the skill of the treating physician.

Several days after the injections she notes substantial improvement in her pain. This gradually improves over a 2 to 3 week period in which she notes increased mobility in her elbow and knee joints. The patient states that the pain is better than at any time in the last 4 years. The improved condition persists for up to 6 months after injection of the neurotoxin.

What is claimed is:

1. A method for treating fibromyalgia, the method comprising the step of administering subcutaneously or intramuscularly a therapeutically effective amount of a *botulinum* toxin to a peripheral location of a body of a patient afflicted with fibromyalgia, wherein the peripheral location is not a locus of pain, and wherein the locus of pain and the site of administration are located within a same dermatome, thereby relieving a fibromyalgia pain for at least one month.

2. The method of claim 1 wherein the peripheral location is in a head of the patient, and wherein the locus of pain is not in the head of the patient.

3. The method of claim 1 wherein the peripheral location is in a head of the patient, and wherein the locus of pain is at a fibromyalgia tender point.

4. The method of claim 1 wherein the peripheral location is in a cranial area or a facial area of the patient, and wherein the locus of pain is at a fibromyalgia tender point.

5. The method of claim 1 wherein the *botulinum* toxin is selected from the group consisting of *botulinum* toxin types A, B, C, D, E, F, and G.

6. The method of claim 1 wherein the *botulinum* toxin is a *botulinum* toxin type A.

7. The method of claim 1 wherein the location of peripheral administration and the locus of pain have neuronal processes that are projected from the same spinal sensory nerve root.

8. The method of claim 1 wherein the *botulinum* toxin is administered with a needle.

9. The method of claim 1 wherein the *botulinum* toxin is administered by needleless injection.

10. A method for treating fibromyalgia pain, the method comprising the step of administering subcutaneously or intramuscularly a therapeutically effective amount of a *botulinum* toxin to a peripheral location of a body of a patient, wherein the patient has a locus of pain at a fibromyalgia tender point, and wherein the peripheral location is not at the locus of pain, and the locus of pain and the site of administration are located within a same dermatome, thereby relieving the pain for at least one month.

11. The method of claim 10 wherein the patient has at least eleven loci of pain.

12. The method of claim 10 wherein the *botulinum* toxin is selected from the group consisting of *botulinum* neurotoxin types A, B, C, D, E, F, and G.

13. The method of claim 10 wherein the *botulinum* toxin is a *botulinum* toxin type A.

14. The method of claim 10 wherein the location of peripheral administration and the locus of pain have neuronal processes that are projected from the same spinal sensory nerve root.

15. The method of claim 10 wherein the *botulinum* toxin is administered with a needle.

16. The method of claim 10 wherein the *botulinum* toxin is administered by needleless injection.

17. A method for treating fibromyalgia, the method comprising the step of administering subcutaneously or intramuscularly a therapeutically effective amount of a *botulinum* toxin to a dermatome of a patient afflicted with fibromyalgia, wherein the dermatome encompasses 50% or more of a locus of pain, wherein the administration is not at the locus of pain, thereby relieving a fibromyalgia pain for at least one month.

18. The method of claim 17 wherein the *botulinum* toxin is selected from the group consisting of *botulinum* toxin types A, B, C, D, E, F, and G.

19. The method of claim 17 wherein the *botulinum* toxin is a *botulinum* toxin type A.

20. The method of claim 17 wherein the location of administration and the locus of pain have neuronal processes that are projected from the same spinal sensory nerve root.

21. The method of claim 17 wherein the *botulinum* toxin is administered with a needle.

22. The method of claim 17 wherein the *botulinum* toxin is administered by needleless injection.

23. A method for treating fibromyalgia pain, the method comprising the step of administering subcutaneously or intramuscularly a therapeutically effective amount of a *botulinum* toxin to a dermatome of a patient, wherein the patient has a locus of pain at a fibromyalgia tender point, wherein the dermatome encompasses 50% or more of the locus of pain, and wherein the administration is not at the locus of pain, thereby relieving the pain for at least one month.

24. The method of claim 23 wherein the patient has at least eleven loci of pain.

25. The method of claim 23 wherein the locus of pain and the peripheral location are located within a dermatome.

26. The method of claim 23 wherein the *botulinum* toxin is selected from the group consisting of *botulinum* neurotoxin types A, B, C, D, E, F, and G.

27. The method of claim 23 wherein the *botulinum* toxin is a *botulinum* toxin type A.

28. The method of claim 23 wherein the location of administration and the locus of pain have neuronal processes that are projected from the same spinal sensory nerve root.

29. The method of claim 23 wherein the *botulinum* toxin is administered with a needle.

30. The method of claim 23 wherein the *botulinum* toxin is administered by needleless injection.

31. A method for treating fibromyalgia, the method comprising the step of administering subcutaneously or intramuscularly a therapeutically effective amount of a *botulinum* toxin type A to a dermatome of a patient afflicted with fibromyalgia, wherein the dermatome encompasses 50% or more of a locus of pain which is at a fibromyalgia tender point, and wherein the local administration is not at the locus of pain, thereby relieving a fibromyalgia pain for at least one month.

32. A method for treating fibromyalgia pain, the method comprising the step of administering subcutaneously or intramuscularly a therapeutically effective amount of a *botulinum* toxin type A to a dermatome of a patient, wherein the patient has a locus of pain which is at a fibromyalgia tender point, wherein the dermatome encompasses 50% or more of the locus of pain, and wherein the administration is not at the locus of pain, thereby relieving the pain for at least one month.

\* \* \* \* \*